United States Patent
Cho et al.

(10) Patent No.: US 8,152,730 B2
(45) Date of Patent: Apr. 10, 2012

(54) METHOD FOR CONTINUOUS BAROREFLEX SENSITIVITY MEASUREMENT

(75) Inventors: Yong K. Cho, Maple Grove, MN (US); Tommy D. Bennett, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/013,465

(22) Filed: Jan. 25, 2011

(65) Prior Publication Data

US 2011/0172544 A1  Jul. 14, 2011

Related U.S. Application Data (63) Continuation of application No. 11/343,635, filed on Jan. 31, 2006, now Pat. No. 7,874,992.

(51) Int. Cl.
*A61B 5/02* (2006.01)

(52) U.S. Cl. ........................................ 600/483; 600/481

(58) Field of Classification Search .................. 600/481, 600/483–486, 529
See application file for complete search history.

(56) References Cited

U.S. PATENT DOCUMENTS

| | | | |
|---|---|---|---|
| 4,791,931 A | 12/1988 | Slate | |
| 5,437,285 A | 8/1995 | Verrier et al. | |
| 6,073,048 A | 6/2000 | Kieval et al. | |
| 6,371,922 B1 | 4/2002 | Baumann et al. | |
| 6,421,557 B1 | 7/2002 | Meyer | |
| 6,506,161 B2 | 1/2003 | Brockway et al. | |
| 2001/0037070 A1 | 11/2001 | Cranley et al. | |
| 2002/0026111 A1 | 2/2002 | Ackerman | |
| 2004/0116784 A1 | 6/2004 | Gavish | |
| 2005/0143779 A1 | 6/2005 | Libbus | |
| 2005/0149143 A1 | 7/2005 | Libbus et al. | |

FOREIGN PATENT DOCUMENTS

| | | |
|---|---|---|
| EP | 0450341 | 10/1991 |
| WO | WO 9515116 | 6/1995 |
| WO | WO 2005/097256 | 10/2005 |

OTHER PUBLICATIONS

Badra, L.J., et al., "Respiratory Modulation of Human Autonomic Rhythms", Am J Physiol Heart Circ Physiol, 2001. 280(6): p. H2674-2688.

La Rovere, M.T., et al., "Baroreflex Sensitivity and Heart Rate Variability in the Identification of Patients at Risk for Life-Threatening Arrhythmias: Implications for Clinical Trials", Circulation, 2001. 103(16): p. 2072-2077.

La Rovere, M.T., et al., "Exercise-Induced Increase in Baroreflex Sensitivity Predicts Improved Prognosis After Myocardial Infarctio", Circulation, 2002. 106(8): p. 945-949.

Lanfranchi, P.A. and V.K. Somers, "Arterial Baroreflex Function and Cardiovascular Variability: Interactions and Implications", Am J Physiol Regul Integr Comp Physiol, 2002. 283(4): p. R815-826.

Halamek, J., et al., "Variability of Phase Shift Between Blood Pressure and Heart Rate Fluctuations: A Marker of Short-Term Circulation Control", Circulation, 2003. 108(3): p. 292-297.

(Continued)

*Primary Examiner* — Patricia Mallari
*Assistant Examiner* — Christian Jang
(74) *Attorney, Agent, or Firm* — Reed A. Duthler (57) ABSTRACT

A medical device and method for determining baroreflex sensitivity (BRS) based on one or more respiration cycles. The BRS determination may be performed continuously based on measurements of heart rate, blood pressure, and respiration cycles.

11 Claims, 5 Drawing Sheets

OTHER PUBLICATIONS

Pinna et al, Applicability and Clinical Relevance of the Transfer Function Method in the Assessment of Baroreflex Sensitivity in Heart Failure Patients, Journal of the American College of Cardiology, Elsevier, New York, NY, US, vol. 46, No. 7 (Oct. 4, 2005), pp. 1314-1321.

Nugent et al, Baroreflex Sensitivity in Children: a Spectral Analysis Evaluation, Engineering in Medicine and Biology Society, Proceedings of the 15th Annual International Conference of the IEEE, (Oct. 28, 1993) pp. 367-368.

Nugent et al, Baroreflex Evaluation in Children at Respiratory Frequencies, Engineering in Medicine and Biology Society, Proceedings of the Annual International Conference of the IEEE, (Oct. 31, 1991), vol. 13, pp. 2341-2342.

International Search Report, PCT/US2007/060853, May 14, 2007, 8 Pages.

METHOD FOR CONTINUOUS BAROREFLEX SENSITIVITY MEASUREMENT

RELATED APPLICATION

This application is a continuation of U.S. patent application Ser. No. 11/343,635, filed Jan. 25, 2011 entitled "METHOD FOR CONTINUOUS BAROREFLEX SENSITIVITY MEASUREMENT", herein incorporated by reference in its entirety.

BACKGROUND

The present invention relates generally to a medical devices, and, more particularly, to implantable medical devices.

Congestive heart failure is a serious condition affecting at least five million Americans. Patients diagnosed with heart failure have an extremely poor long-term prognosis. The average life expectancy of a person suffering from chronic heart failure is approximately five years. Because of the severity of chronic heart failure, a need exists for developing efficacious therapies for this disease. The patient's clinical and hemodynamic status determines the baroreflex sensitivity (BRS), which is a measure of the ability of that individual's heart to react to changes in blood pressure by changing heart rate. The BRS of a chronic heart failure patient parallels that patient's clinical and hemodynamic status. Thus, BRS provides an indicator for the efficacy of a drug therapy or a ventricular resynchronization therapy. BRS may also be used to predict arrhythmic events and mortality in these patients.

In recent years, autonomic markers such as heart rate variability (HRV) and BRS have been recognized as a good indicator of a deteriorating heart. While HRV deals with the changes in the RR interval as a single variable, BRS measures the relationship between input and output signals in a feedback system. Typically, BRS takes systolic blood pressure as an input and RR interval as an output. Several methods have been suggested to measure BRS such as bolus injection of vasoactive drugs (e.g., phenylephrine), the Valsalva maneuver, and mechanical alteration of transmural carotid sinus pressure by means of the neck chamber. Such past techniques merely provide a snapshot in time of BRS and the results of such BRS tests must be compared against test results of other patients in order to determine whether the BRS indicate a worsening heart failure condition.

DESCRIPTION OF VARIOUS EMBODIMENTS

The following discussion is presented to enable a person skilled in the art to make and use embodiments of the invention. Various modifications to the illustrated embodiments will be readily apparent to those skilled in the art, and the generic principles herein may be applied to other embodiments and applications without departing from embodiments of the invention. Thus, embodiments of the invention are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of embodiments of the invention. Skilled artisans will recognize the examples provided herein have many useful alternatives and fall within the scope of embodiments of the invention. The following introductory material is intended to familiarize the reader with the general nature and some of the features of embodiments of the invention.

Certain embodiments of the invention may include, or may be adapted for use in, diagnostic monitoring equipment, external medical device systems, and implantable medical devices (IMDs), including implantable hemodynamic monitors (IHMs), implantable cardioverter-defibrillators (ICDs), cardiac pacemakers, cardiac resynchronization therapy (CRT) pacing devices, drug delivery devices, or combinations of such devices.

Figure 1:
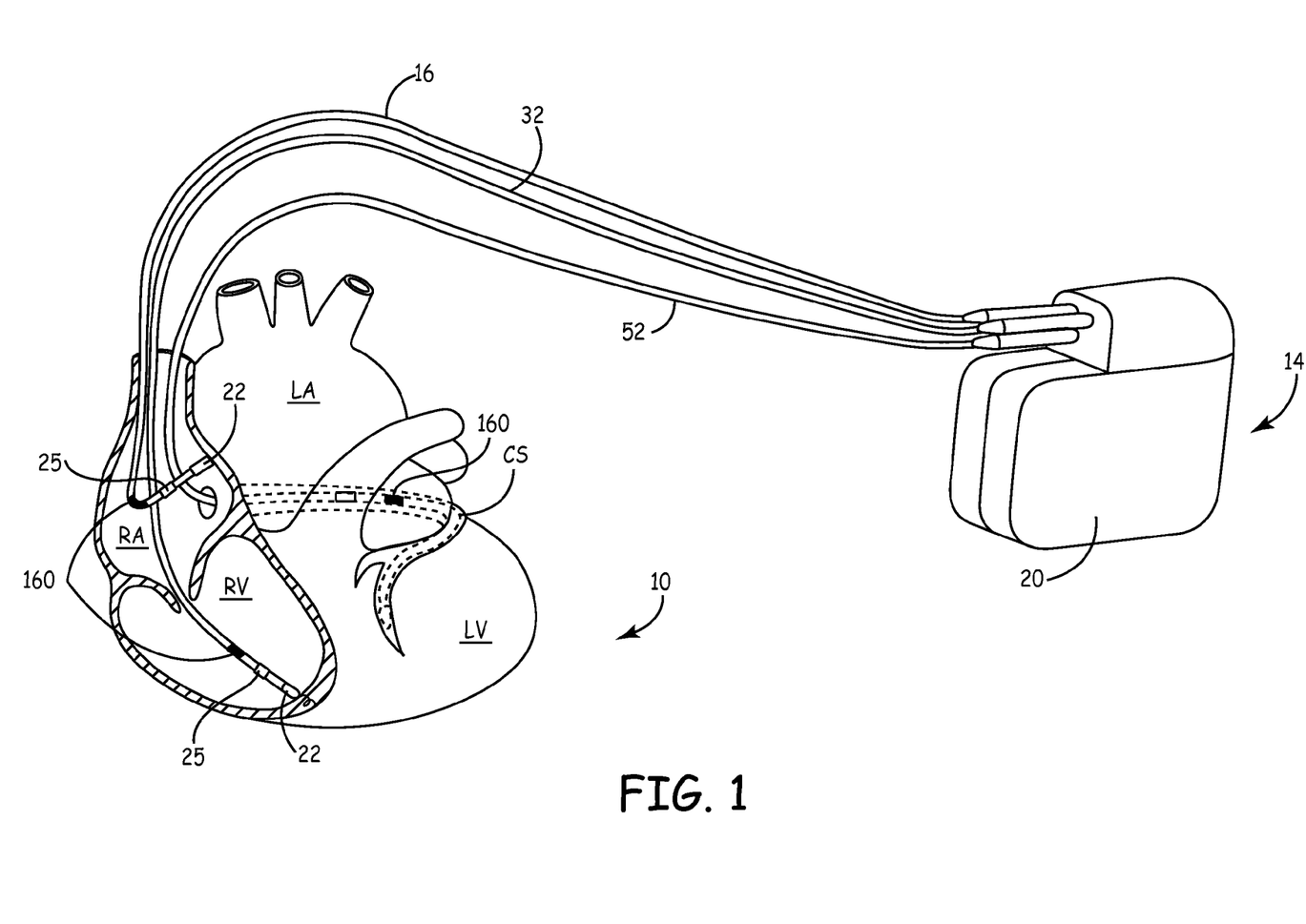
FIG. 1 is a schematic diagram depicting a multi-channel, atrial and bi-ventricular, monitoring/pacing IMD in which embodiments of the invention may be implemented.

FIG. 1 is a schematic representation of an IMD 14 that may be used in accordance with certain embodiments of the invention. The IMD 14 may be any device that is capable of measuring hemodynamic parameters (e.g., blood pressure signals) from within a ventricle of a patient's heart, and which may further be capable of measuring other signals, such as the patient's electrogram (EGM).

In FIG. 1, heart 10 includes the right atrium (RA), left atrium (LA), right ventricle (RV), left ventricle (LV), and the coronary sinus (CS) extending from the opening in the right atrium laterally around the atria to form the great vein.

FIG. 1 depicts IMD 14 in relation to heart 10. In certain embodiments, IMD 14 may be an implantable, multi-channel cardiac pacemaker that may be used for restoring AV synchronous contractions of the atrial and ventricular chambers and simultaneous or sequential pacing of the right and left ventricles. Three endocardial leads 16, 32 and 52 connect the IMD 14 with the RA, the RV and the LV, respectively. Each lead has at least one electrical conductor and pace/sense electrode, and a can electrode 20 may be formed as part of the outer surface of the housing of the IMD 14. The pace/sense electrodes and can electrode 20 may be selectively employed to provide a number of unipolar and bipolar pace/sense electrode combinations for pacing and sensing functions. The depicted positions in or about the right and left heart chambers are merely exemplary. Moreover other leads and pace/sense electrodes may be used instead of the depicted leads and pace/sense electrodes.

It should be noted that the IMD 14 may also be an ICD, a CRT device, an IHM, or any other such device or combination of devices (e.g., a neurological stimulator, a drug pump or the like), according to various embodiments of the invention.

Typically, in pacing systems of the type illustrated in FIG. 1, the electrodes designated above as "pace/sense" electrodes are used for both pacing and sensing functions. In accordance with one aspect of the present invention, these "pace/sense" electrodes can be selected to be used exclusively as pace or sense electrodes or to be used in common as pace/sense electrodes in programmed combinations for sensing cardiac signals and delivering pace pulses along pacing and sensing vectors.

In addition, some or all of the leads shown in FIG. 1 could carry one or more pressure sensors for measuring systolic and diastolic pressures, and a series of spaced apart impedance sensing leads for deriving volumetric measurements of the expansion and contraction of the RA, LA, RV and LV.

The leads and circuitry described above can be employed to record EGM signals, blood pressure signals, and impedance values over certain time intervals. The recorded data may be periodically telemetered out to a programmer operated by a physician or other healthcare worker in an uplink telemetry transmission during a telemetry session, for example.

Figure 2:
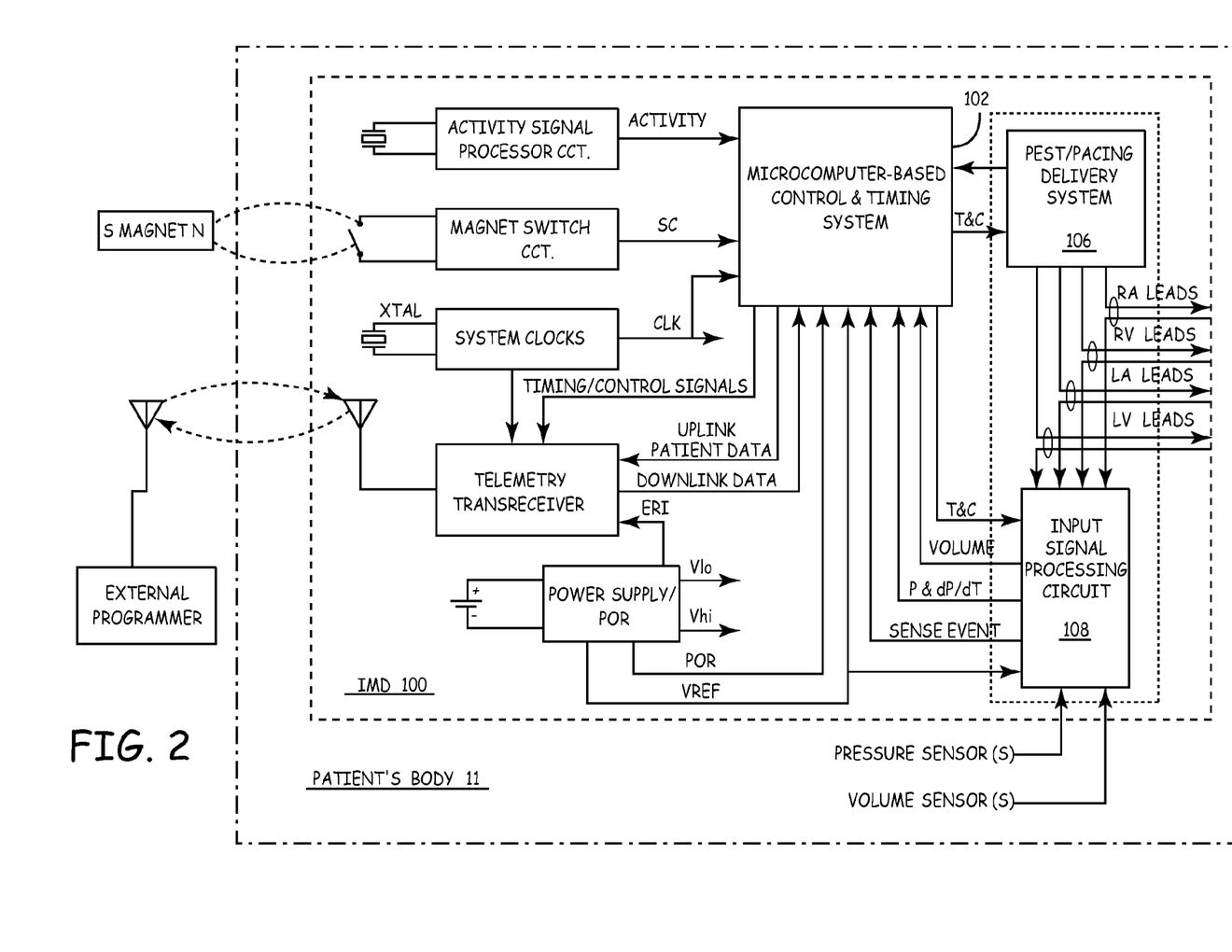
FIG. 2 is a simplified block diagram of an embodiment of IMD circuitry and associated leads that may be employed in the system of FIG. 1 enabling selective therapy delivery and monitoring in one or more heart chamber.

FIG. 2 depicts a system architecture of an exemplary multi-chamber monitor/sensor 100 implanted into a patient's body 11 that provides delivery of a therapy and/or physiologic input signal processing. The typical multi-chamber monitor/sensor 100 has a system architecture that is constructed about a microcomputer-based control and timing system 102 which varies in sophistication and complexity depending upon the type and functional features incorporated therein. The functions of microcomputer-based multi-chamber monitor/sensor control and timing system 102 are controlled by firmware and programmed software algorithms stored in RAM and ROM including PROM and EEPROM and are carried out using a CPU or ALU of a typical microprocessor core architecture.

The therapy delivery system 106 can be configured to include circuitry for delivering cardioversion/defibrillation shocks and/or cardiac pacing pulses delivered to the heart or cardiomyostimulation to a skeletal muscle wrapped about the heart. Alternately, the therapy delivery system 106 can be configured as a drug pump for delivering drugs into the heart to alleviate heart failure or to operate an implantable heart assist device or pump implanted in patients awaiting a heart transplant operation.

The input signal processing circuit 108 includes at least one physiologic sensor signal processing channel for sensing and processing a sensor derived signal from a physiologic sensor located in relation to a heart chamber or elsewhere in the body. Examples illustrated in FIG. 2 include pressure and volume sensors, but could include acceleration, oxygen saturation, or spatial sensors.

Figure 3:
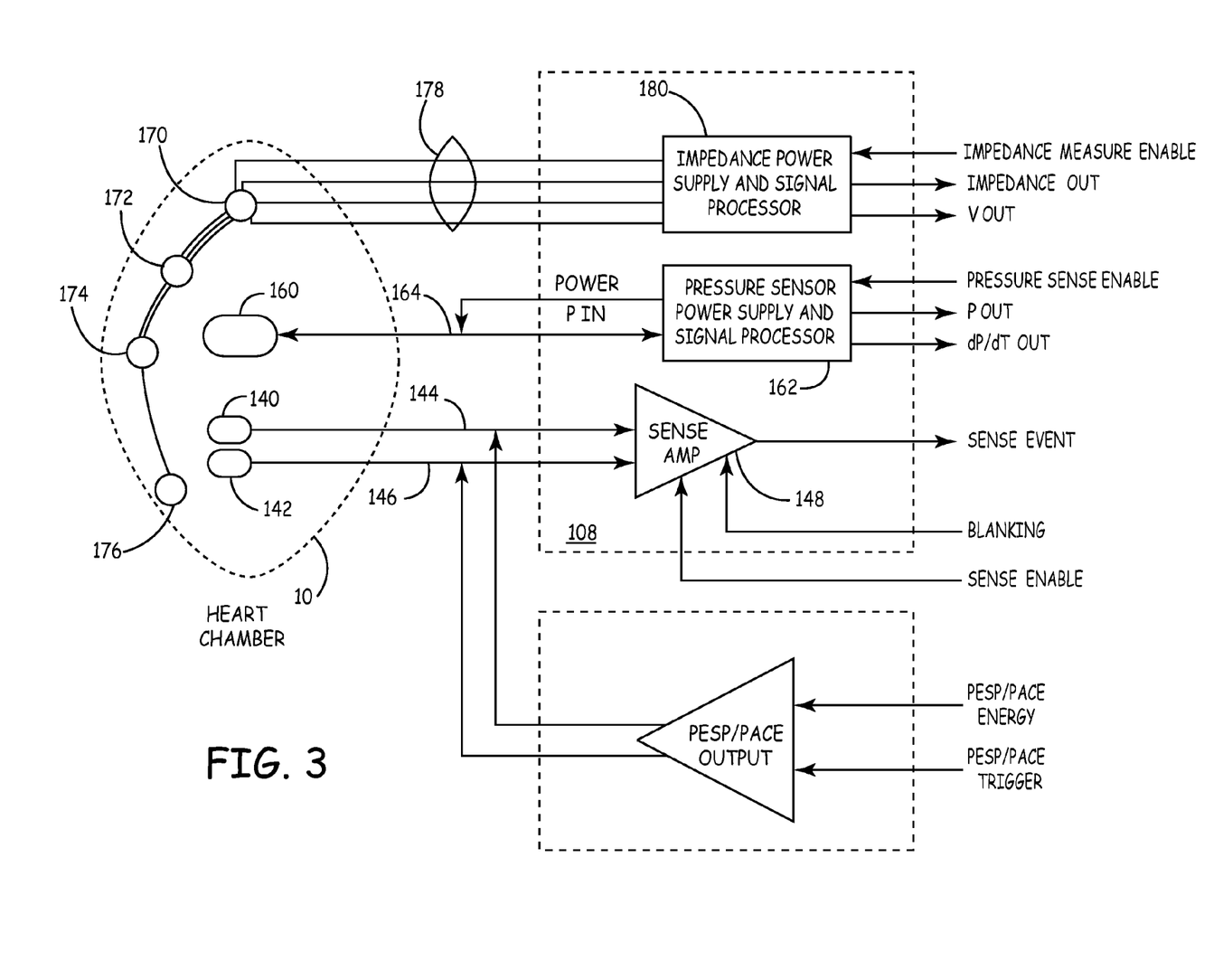
FIG. 3 is a simplified block diagram of a single monitoring and pacing channel for acquiring pressure, impedance and cardiac EGM signals employed in monitoring cardiac functioning and/or delivering therapy, including pacing therapy, in accordance with embodiments of the invention.

FIG. 3 schematically illustrates one pacing, sensing and parameter measuring channel in relation to one heart chamber. A pair of pace/sense electrodes 140, 142, a pressure sensor 160, and a plurality, e.g., four, impedance measuring electrodes 170, 172, 174, 176 are located in operative relation to the heart 10.

The pair of pace/sense electrodes 140, 142 are located in operative relation to the heart 10 and coupled through lead conductors 144 and 146, respectively, to the inputs of a sense amplifier 148 located within the input signal processing circuit 108. The sense amplifier 148 is selectively enabled by the presence of a sense enable signal that is provided by control and timing system 102. The sense amplifier 148 is enabled during prescribed times when pacing is either enabled or not enabled in a manner known in the pacing art. The blanking signal is provided by control and timing system 102 upon delivery of a pacing pulse or pulse train to disconnect the sense amplifier inputs from the lead conductors 144 and 146 for a short blanking period in a manner well known in the art. The sense amplifier provides a sense event signal signifying the contraction of the heart chamber commencing a heart cycle based upon characteristics of the EGM. The control and timing system responds to non-refractory sense events by restarting an escape interval (EI) timer timing out the EI for the heart chamber, in a manner well known in the pacing art.

The pressure sensor 160 is coupled to a pressure sensor power supply and signal processor 162 within the input signal processing circuit 108 through a set of lead conductors 164. Lead conductors 164 convey power to the pressure sensor 160, and convey sampled blood pressure signals from the pressure sensor 160 to the pressure sensor power supply and signal processor 162. The pressure sensor power supply and signal processor 162 samples the blood pressure impinging upon a transducer surface of the sensor 160 located within the heart chamber when enabled by a pressure sense enable signal from the control and timing system 102. Absolute pressure (P), developed pressure (DP) and pressure rate of change (dP/dt) sample values can be developed by the pressure sensor power supply and signal processor 162 or by the control and timing system 102 for storage and processing.

A variety of hemodynamic parameters may be recorded, for example, including right ventricular (RV) systolic and diastolic pressures (RVSP and RVDP), estimated pulmonary artery diastolic pressure (ePAD), pressure changes with respect to time (dP/dt), heart rate, activity, and temperature. Some parameters may be derived from others, rather than being directly measured. For example, the ePAD parameter may be derived from RV pressures at the moment of pulmonary valve opening, and heart rate may be derived from information in an intracardiac electrogram (EGM) recording. Pressure sensor 160 may be used to sense the pressure data, but it is contemplated that most any type of sensor could be used, such as an external cuff sensor, implantable pressure sensor, or a flow sensor in the venous or arterial system, without departing from the spirit of the invention. Further, the blood pressure can be detected most anywhere in the body including other chambers of the heart without departing from the spirit of the invention.

The set of impedance electrodes 170, 172, 174 and 176 is coupled by a set of conductors 178 and is formed as a lead that is coupled to the impedance power supply and signal processor 180. Impedance-based measurements of cardiac parameters such as stroke volume are known in the art, such as an impedance lead having plural pairs of spaced surface electrodes located within the heart 10. The spaced apart electrodes can also be disposed along impedance leads lodged in cardiac vessels, e.g., the coronary sinus and great vein or attached to the epicardium around the heart chamber. The impedance lead may be combined with the pace/sense and/or pressure sensor bearing lead.

The data stored by IMD 14 may include continuous monitoring of various parameters, for example recording intracardiac EGM data at sampling rates as fast as 256 Hz or faster. In certain embodiments of the invention, an IHM may alternately store summary forms of data that may allow storage of data representing longer periods of time. In one embodiment, hemodynamic pressure parameters may be summarized by storing a number of representative values that describe the hemodynamic parameter over a given storage interval. The mean, median, an upper percentile, and a lower percentile are examples of representative values that may be stored by an IHM to summarize data over an interval of time (e.g., the storage interval). In one embodiment of the invention, a storage interval may contain six minutes of data in a data buffer, which may be summarized by storing a median value, a 94th percentile value (i.e., the upper percentile), and a 6th percentile value (i.e., the lower percentile) for each hemodynamic pressure parameter being monitored. In this manner, the memory of the IHM may be able to provide weekly or monthly (or longer) views of the data stored. The data buffer, for example, may acquire data sampled at a 256 Hz sampling rate over a 6 minute storage interval, and the data buffer may be cleared out after the median, upper percentile, and lower percentile values during that 6 minute period are stored. It should be noted that certain parameters measured by the IHM may be summarized by storing fewer values, for example storing only a mean or median value of such parameters as heart rate, activity level, and temperature, according to certain embodiments of the invention.

Although various stimuli can be utilized to assess BRS, certain embodiments of the present invention provide for a continuous measurement of BRS. As explained further below, one convenient triggering mechanism for BRS measurement is respiration since it provides a continuous and periodic perturbation of the autonomic nervous system.

An increase in heart rate is typically associated with an increase in blood pressure up to a certain point where the signals start to deviate. Similarly, as pressure decreases, heart rate typically decreases. In patients with heart failure, however, blood pressure and heart rate do not track together very well. As the patient's heart failure worsens, the patient's tracking of blood pressure and heart rate also worsens.

BRS is a measure of the ability of that individual's heart to react to changes in blood pressure by changing heart rate. Baroreflex sensitivity measures the state of autonomic nervous system, thus the balance of the sympathetic and parasympathetic.

The "respiration effect" may be used as one convenient basis for measuring BRS. Cardiac function varies during respiration, a phenomenon referred to as the "respiration effect." Pressures in the right atrium and thoracic vena cava depend on intrapleural pressure ($P_{pl}$). During inspiration, the vagus nerve activity is impeded and heart rate increases. Also, the chest wall expands and the diaphragm lowers. This causes a fall in $P_{pl}$ that leads to expansion of the lungs and cardiac chambers (e.g., right atrium and right ventricle), and a reduction in right atrial and ventricular pressures. As right atrial pressure falls during inspiration, the pressure gradient for venous return to the right ventricle increases. During expiration, the opposite occurs. The degree of heart rate fluctuation is also controlled by regular impulses from the baroreceptors (pressure sensors) in the aorta and carotid arteries as well as cardiopulmonary receptors. Respiration provides a convenient basis for measuring BRS since the perturbation of blood pressure and resulting change in heart rate may be used as inputs for a continuous BRS measurement. The pressure decrease during inspiration typically induces a heart rate increase. The pressure increase during expiration typically induces a heart rate decrease. BRS is a measure of the ability of that individual's heart to react to changes in blood pressure during respiration by changing heart rate.

Methods and systems in accordance with certain embodiments of the invention may therefore include monitoring of the respiratory cycle (inspiration and expiration) for use as the basis for continuous BRS measurement. To date, various methods have been proposed for detecting respiration in an IMD. For example, minute ventilation sensors have been used to measure respiration by monitoring cyclic changes in transthoracic impedance that occur during respiration. Intracardiac electrogram (EGM) amplitude modulation has also been used to monitor respiration. A technique for monitoring respiration that uses blood pressure signals has also been proposed.

Certain embodiments of the present invention also collect pressure measurements and heart rate information for use in continuous BRS measurement. Such pressure measurements may include RVDP and RVSP, as well as parameters that may be derived from other pressure parameters, such as estimated pulmonary artery diastolic pressure (ePAD) and rate of pressure change (dP/dt). Moreover, corresponding left side pressures, such as LVSP, LVDP, LVPP, LAP, or RAP, may also be used in BRS measurement.

In more specific embodiments, hemodynamic data for continuous BRS assessment is gathered using a lead located in the right ventricle. In these specific embodiments, the lead can measure pressure based on RV pressure and heart rate based on RR interval length. BRS assessment can be achieved using spontaneous respiratory effort as the stimulus by calculating the ratio between the change in RR interval and the change in RV pressure parameters (e.g., RV systolic pressure). The following equation describes the concept.

$$\text{Continuous} \frac{\Delta RR \text{ (ms)}}{\Delta RVSP \text{ (mmHg)}}$$

$\Delta$RR represents the difference in the maximum RR interval and the minimum RR interval for the time period in question. $\Delta$RVSP represents the difference in the maximum RV systolic pressure and the minimum RV systolic pressure for the same time period. These maximum and minimum values usually occur at the beginning of a respiration cycle (minimum tidal volume) and at the end inspiration (peak tidal volume), respectively.

BRS can be determined over many different time periods. For instance, in one embodiment, BRS is calculated for each respiration cycle. That is, the maximum and minimum RR intervals and RVSP are determined for each respiration cycle. In other embodiments, BRS is calculated over just the inspiration period or just the expiration period. BRS can also be estimated on a beat-to-beat basis at every cardiac cycle using the equation provided above. In such an embodiment, $\Delta$RR and $\Delta$RVSP are just values calculated from two most recent samples of RR interval and RVSP, and it is not necessary to determine respiration cycles prior to BRS calculation. As noted above, pressure changes other than RVSP may be used. Such pressure changes may be substituted for $\Delta$RVSP in the equation above. In certain embodiments, $\Delta$RR and $\Delta$RVSP in the BRS calculation can be measured over different respiration cycles, as indicated by the following equation.

$$\text{Continuous\_BRS=}$$

In these embodiments, $(\Delta RR)_{t-n}$ represents the difference in the maximum RR interval and the minimum RR interval for the respiration cycle (t-n), where t is the current respiration cycle and n (which may be equal to 0, 1, 2, 3 ...) is the number of respiration cycles ago in which the $\Delta$RR value should be calculated. Similarly, $(\Delta RVSP)_{t-m}$ represents the difference in the maximum RV systolic pressure and the minimum RV systolic pressure for respiration cycle (t-m), where t is again the current respiration cycle and m (which may be equal to 0, 1, 2, 3 ...) is the number of respiration cycles ago in which the $\Delta$RVSP should be calculated. Basing the BRS measurement off of different respiration cycles (i.e., n not equal to m) provides a BRS measurement that accounts for delays between a change in one variable and an effect on the other variable. For instance, as noted above, respiration causes pressure changes such as a change in RVSP. It may take several respiration cycles for the pressure change to physiologically induce a rate change, such as a change in RR. Using the equation above with, for instance, n=0 and m=3, the BRS calculation can account for a delay of 3 respiration cycles between the ΔRR induced in the (t−0) current respiratory cycle by the ΔRVSP from the (t−3) respiration cycle 3 cycles ago. The values of m and n may be predetermined, preprogrammed, or set to change dynamically based on data from device sensors.

Figure 4A:
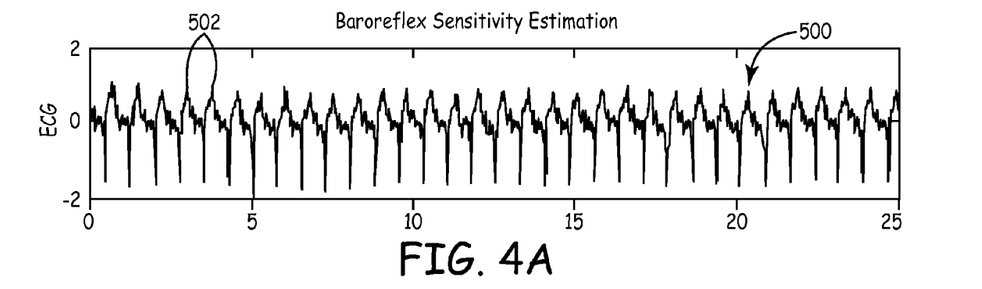
FIG. 4A illustrates a plot of a patient ECG signal over time.
Figure 4B:
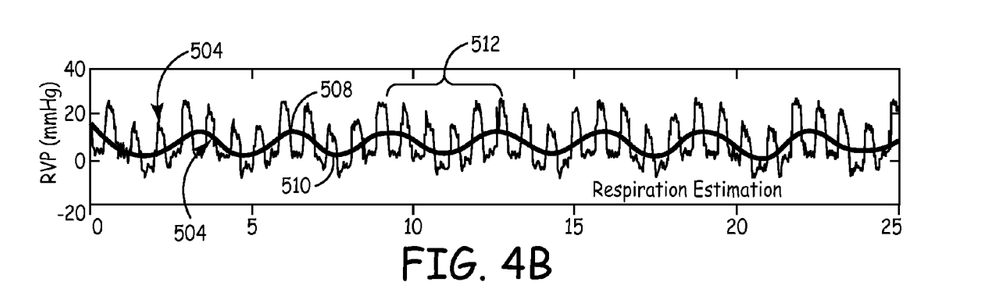
FIG. 4B shows a plot of a right ventricle systolic pressure measurement and a respiration waveform over the same time frame as FIG. 4A.
Figure 4C:
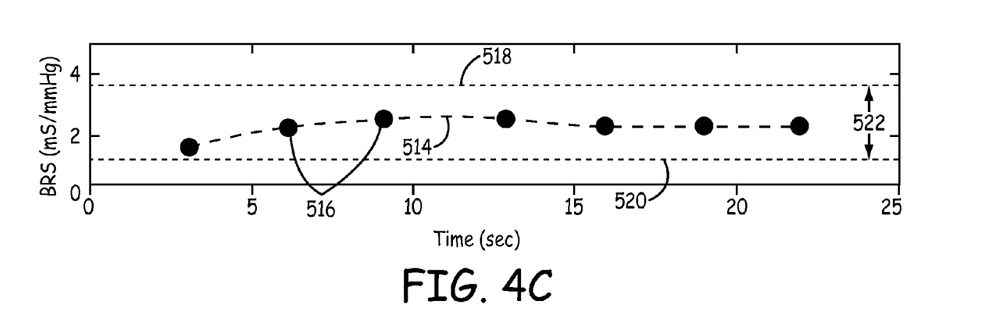
FIG. 4C illustrates a plot of the baroreflex sensitivity values determined from the hemodynamic data illustrated as FIGS. 4A and 4B.

FIGS. 4A-4C graphically illustrate plots of hemodynamic data used to continuously estimate BRS. FIG. 4A illustrates a plot of a patient ECG signal 500 over time used in a BRS calculation. In this plot, exemplary RR interval 502 is shown. It is understood, of course, that an EGM signal could be used instead of or in addition to ECG signal 500.

Detection of respiration is, of course, required in order to estimate BRS for a given respiration cycle. In one embodiment, respiration is detected using RV pressure signals. FIG. 4B shows a plot of an RV systolic pressure 504 measurement (RVSP) of the patient over the same time frame as FIG. 4A. As mentioned above, other pressure measurements could be used instead or in addition to RVSP 504. A sensor, such as pressure sensor 160 (FIG. 3), may be used to sense RVSP. FIG. 4B also shows a respiration waveform 506 superimposed over RVSP 504. Respiration waveform 506 may be derived by passing the RVSP signal 504 through a low-pass filter such that higher frequency components may be filtered out or removed. Other methods and mechanisms may be substituted in order to detect respiration without departing from the spirit of the invention. For instance, various sensor combinations can be employed, such as impedance, $O_2$, piezoelectric sensors. Additionally, pressure waveforms, other than RVSP, may be used to help detect respiration.

Peaks 508 of respiration waveform 506 in FIG. 4B occur with high RVSP and correspond with the end of expiration and beginning of inspiration. Troughs 510 of respiration waveform 506 occur with low RVSP and correspond with the end of inspiration and beginning of expiration. Accordingly, a single respiration cycle 512 may also be seen from respiration waveform 506. Of course, a respiration cycle may be considered to run from beginning inspiration to end expiration (as shown as 512) or from beginning expiration to end inspiration. Using the data from FIGS. 4A and 4B, BRS may be calculated continuously, for instance, over each respiration cycle 512, by determining the greatest change in RR intervals and RVSP.

FIG. 4C illustrates a plot 514 of the individual BRS values 516 determined from the hemodynamic data illustrated as FIGS. 4A and 4B. BRS data can be stored in the device memory or transmitted to an external storage device using telemetry as discussed in detail above. By continuously measuring BRS, the BRS values 516 may be monitored for changes over time. As indicated above, a deteriorating BRS can signal worsening heart failure. Past methods of BRS determination, which provided a one-time measurement, were difficult to compare against other since the tests were sporadic and irregular.

In addition to comparing BRS measurements against each other, BRS measurements may be monitored and trended to see whether they remain within an envelope of predetermined thresholds. FIG. 4C shows an upper threshold 518 (shown as approximately 3.5 mS/mmHg) and a lower threshold 520 (shown as approximately 1.5 mS/mmHg), providing a zone 522. For instance, continuous BRS values may be stored and trended over a period of time (e.g., 24 hours). Various techniques can be employed to compose trend data. For example, trend data points may be calculated from median or mean values of any given time duration, or the data points could be smoothed via a low-pass filter smoothing function. The trend may be analyzed to determine whether it increases higher than an upper threshold 518, in which case the patient's condition may have deteriorated to a clinically significant level that may necessitate further investigation or remedial action. In certain embodiments, an alarm is sounded, a therapy is delivered, or a medical professional could be alerted (via a wireless transmission from the implanted medical device) if the trendline 514 of BRS measurements 516 fall above, below, or outside of zone 522. By using a trendline, one measurement will not typically activate an alarm on the IMD. With respect to possible therapies when BRS trendline falls outside of the threshold zone 522, it is contemplated that the IMD could administer a CRT, CPT, or PESP therapy. The therapy would be intended to improve the patient's hemodynamics, thus reducing the effects of the heart failure and hopefully return BRS measurements 516 back within zone 522.

The threshold values 518 and 520 are merely exemplary and are based upon the particular patient and the particular placement of pressure sensor 160. These values may be set during the implant process or during post-implant programming. The values can be based on initial BRS measurements. Upper threshold 518 and lower threshold 520 can also be dynamically changing thresholds. For example, if the IMD obtains BRS measurements that fluctuate above of below the zone 522, then processor 102 can decide to dynamically change upper threshold 518 or lower threshold 520 to account for these fluctuating measurements.

In certain embodiments, continuous BRS measurements are collected and compared under similar patient circumstances, such as similar activity levels. In such embodiments, the IMD determines that such circumstances exist when classifying the BRS measurement data for comparison and trending with past BRS measurement data. Different categories of circumstances include, without limitation, patient activity, time of day, and patient body posture. For instance, in these embodiments, IMD separates BRS measurements into those taken during active periods and periods of inactivity. By doing so, comparisons between BRS measurements can be made under similar patient circumstances.

For instance, in one embodiment where patient circumstances are considered, an activity sensor is used to determine patient activity level. The sensor may sense, for instance, a threshold activity level (e.g., a particular activity count) that triggers the BRS measurement.

In another embodiment, BRS measurements can be triggered by different sensor information. That is, detection of one or more of the patient circumstances noted above may be used as a triggering event to initiate BRS measurements over one or more respiration cycles. For example, a level of exercise can be measured using an activity sensor. When activity level exceeds a pre-determined threshold (e.g., activity counts >6), BRS measurement can begin and continue over respiration cycles until, for instance, the activity level reaches a pre-determined "stop" rate, or a pre-programmed "time" expires (e.g., minutes after trigger).

Posture changes perturbate the autonomic nervous system and can provide a triggering event for continuous BRS measurement. A sensed posture change could then be used to initiate BRS measurement. An accelerometer is one example of a sensor that may be used to sense patient posture changes. For example, if the patient stands up it is expected that the systolic pressure will increase, and if the patient is at rest, then it is expected the systolic pressure would decrease. Knowing this, the algorithm above could be used to calculate the BRS over respiration cycles until, for instance, patient posture changes or a pre-programmed time expires. However, it is fully contemplated that any naturally occurring perturbation of the autonomic system, such as respiration, posture, patient activity, body temperature, could be used without departing from the spirit of the invention. It is further contemplated that other non-naturally occurring events, such as a CRT, a post extra-systolic potentiation (PESP) therapy, or an internally delivered drug therapy could be used as the triggering event without departing from the spirit of the invention.

Figure 5:
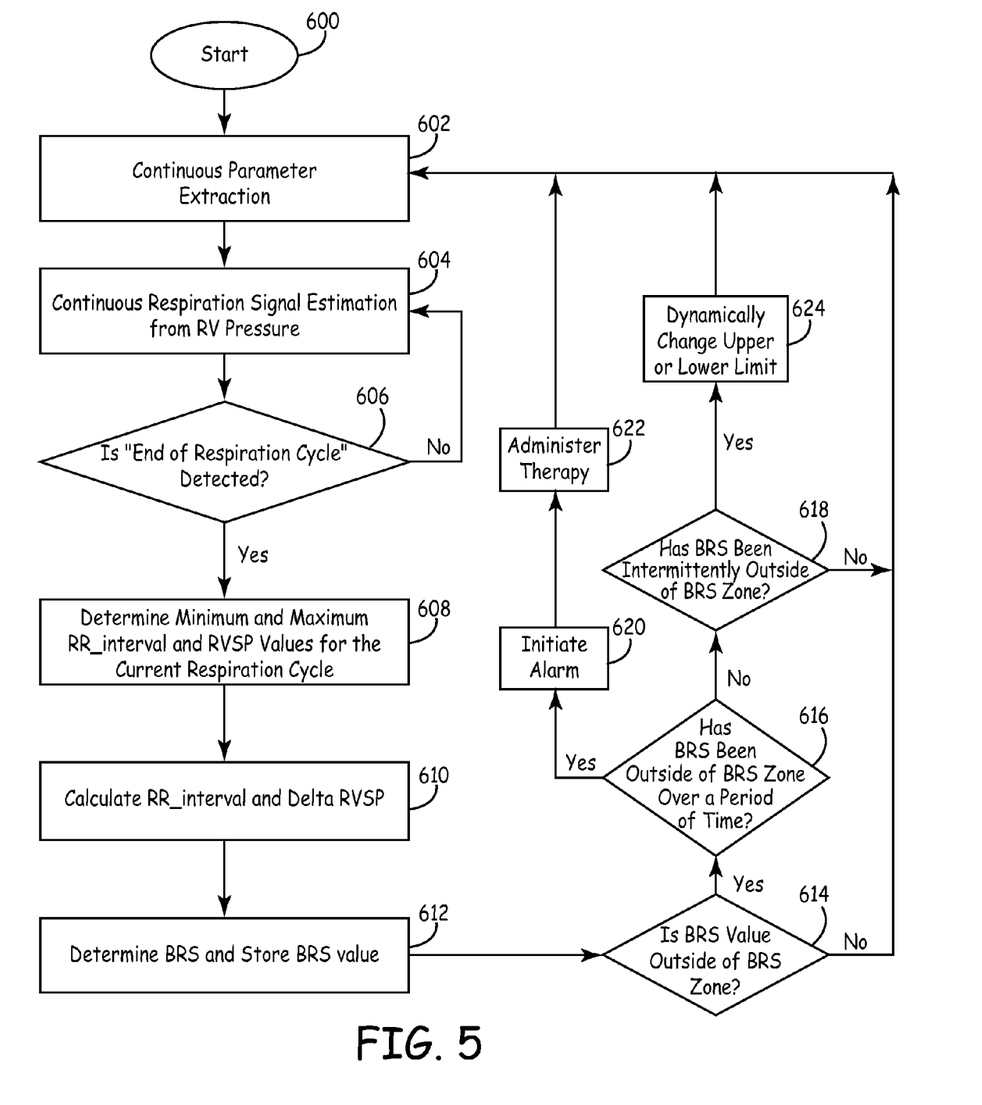
FIG. 5 is a flow chart diagram of a method of obtaining BRS measurements in an embodiment of the present invention.

With reference to FIG. 5, a flow chart diagram of a method of obtaining BRS measurements in an embodiment of the present invention is shown. Processor 102 begins the program at state 600. In the embodiment shown, the program commences immediately. However, initiation of the program could be based upon a sensed perturbation of the autonomic system as discussed above. At state 602, processor 102 begins to collect and store in memory cardiac data including R-R value 502 from an EGM measurement collected by the leads referenced above in FIG. 2 and systolic pressure from the right ventricle as shown in FIG. 4B. At state 604, processor 102 derives a respiration signal based upon the right ventricular pressure utilizing, for example, a lowpass filter that produces a respiration waveform 506 as shown in FIG. 4B. At state 606, processor 102 determines whether the end of a respiration cycle has been detected. If not, then processor returns to state 604. If the end of respiration cycle is detected, then processor 102 proceeds to state 608 to determine the minimum and maximum R-R interval and RVSP values for the current respiration cycle. At state 610, processor 102 calculates the R-R interval and the RVSP. At state 612, processor 102 calculates the BRS utilizing the algorithm discussed above and stores the BRS value in memory.

At state 612, processor 102 determines if the BRS value is outside of zone 522. If the value is outside of zone 522, processor 102 then determines whether the BRS has been outside of zone 522 greater than a predetermined time, for example 2-3 days at state 616. If the value is not outside of zone 522, then processor 102 returns to state 602. If the BRS value has not been outside of zone 522 for greater than the predetermined time frame, then processor 102 proceeds to state 618 to determine to determine if the out of zone 522 values are intermittent. If the BRS values have been outside of zone 522 for over the predetermined time frame, then an alarm is initiated at state 620. Optionally, processor 102 can also administer a therapy, as discussed above, at state 622 to try and improve the hemodynamic performance of the heart. Processor 102 then returns to state 602 once the alarm has been cleared. If the BRS value has been intermittently outside of zone 522, then processor 102 can dynamically change either upper threshold 518 or lower threshold 520 depending on whether the BRS value is intermittently high or low at state 624. If it is determined that the BRS value is not intermittently outside of zone 522, for example, only up to 5 or 10 occurrences have been outside zone 522, then processor 102 proceeds to state 602 to being the process all over again.

Thus, embodiments of the METHOD FOR CONTINUOUS BAROREFLEX SENSITIVITY MEASUREMENT are disclosed. One skilled in the art will appreciate that the present invention can be practiced with embodiments other than those disclosed. The disclosed embodiments are presented for purposes of illustration and not limitation, and the present invention is limited only by the claims that follow.

The invention claimed is:

1. An implantable medical device, comprising:
   one or more sensors for measuring patient heart rate, blood pressure, and respiration cycles; and
   a housing supporting a processor and adapted for implantation in a patient, the processor coupled to the one or more sensors, the processor configured for calculating a baroreflex sensitivity (BRS) value based on heart rate and pressure measurements taken over different respiration cycles.

2. A device according to claim 1, wherein the respiration cycles are detected from the pressure measurements.

3. A device according to claim 1, wherein the measuring the pressure measurements comprise measuring a right ventricular systolic pressure measurements.

4. A device according to claim 1 wherein calculating the BRS value includes determining a maximum change in the pressure metric over each respiration cycle.

5. A device according to claim 1, wherein calculating the BRS value includes determining a maximum change in an R-R interval over each respiration cycle.

6. A device according to claim 1, wherein the heart rate is measured from an ECG signal.

7. A method of monitoring baroreflex sensitivity (BSR), comprising:
   implanting one or more sensors for sensing patient heart rate, blood pressure, and respiration cycles; and
   implanting a housing supporting a processor and adapted for implantation in a patient, the processor coupled to the one or more sensors;
   employing the processor configured to calculate continuous baroreflex sensitivity (BRS) for each detected respiration cycle based on the sensed heart rate, blood pressure and respiration cycles, wherein:
   employing the processor to compare the BRS calculation against a zone of predetermined BRS thresholds, and
   employing the processor to change at least one zone threshold if the BRS calculation intermittently produces values outside the zone.

8. A method according to claim 7, wherein the respiration cycles and blood pressure are sensed by the same one of the one or more sensors.

9. A method according to claim 7, wherein the processor calculates a trendline of BRS values obtained over multiple respiration cycles.

10. A method according to claim 7, wherein the processor initiates an alarm if the BRS calculation is outside the zone of predetermined BRS thresholds.

11. A method according to claim 7, wherein the processor initiates a treatment if the BRS calculation is outside of the zone of predetermined thresholds.

* * * * *